United States Patent [19]
Tsushima et al.

[11] Patent Number: 6,036,974
[45] Date of Patent: Mar. 14, 2000

[54] METHOD AND APPARATUS FOR PREPARATION OF MOLDED TABLET AND THEREBY PREPARED MOLDED TABLET

[75] Inventors: Yuki Tsushima, Honlyo; Kazuhide Ashizawa, Taukuba; Sumio Watanabe, Aichi-ken, all of Japan

[73] Assignee: Eisai Co. Ltd., Tokyo, Japan

[21] Appl. No.: 08/127,555

[22] Filed: Sep. 28, 1993

[30] Foreign Application Priority Data

| Oct. 2, 1992 | [JP] | Japan | 4-287037 |
| Dec. 2, 1992 | [JP] | Japan | 4-345115 |
| Sep. 22, 1993 | [JP] | Japan | 5-236266 |

[51] Int. Cl.$^7$ .................. A61K 9/20; A61J 3/10
[52] U.S. Cl. .................. 424/464; 424/465; 424/466
[58] Field of Search .................. 424/464, 435, 424/465, 466; 426/389, 512

[56] References Cited

U.S. PATENT DOCUMENTS

| 3,789,119 | 1/1974 | Fusari et al. | 514/777 |
| 4,004,036 | 1/1977 | Schmitt | 426/285 |
| 4,091,091 | 5/1978 | Terrill | 514/509 |
| 4,297,350 | 10/1981 | Babcock et al. | 514/172 |
| 4,946,684 | 8/1990 | Blank et al. | 424/441 |
| 5,082,666 | 1/1992 | Rene et al. | 424/467 |
| 5,082,667 | 1/1992 | Van Scoik | 424/465 |
| 5,223,264 | 6/1993 | Wehling et al. | 424/466 |
| 5,603,880 | 2/1997 | Kato et al. | 264/112 |
| 5,672,364 | 9/1997 | Kato et al. | 425/89 |

FOREIGN PATENT DOCUMENTS

| 2576840 | 8/1986 | France . |
| 2197197 | 5/1988 | United Kingdom . |

OTHER PUBLICATIONS

Ansel, Howard C., *Pharmaceutical Dosage Forms and Drug Delivery Systems*, 5$^{th}$ ed., Lea & Febiger, Philadelphia, 1990, p.160.

*Remington's Pharmaceutical Sciences*, 18$^{th}$ ed., Mack Publishing Co., Easton, Pa, 1990 pp. 1656–1658.

*Primary Examiner*—Robert H. Harrison
*Attorney, Agent, or Firm*—Griffin, Butler, Whisenhunt & Szipl, LLP

[57] ABSTRACT

Active ingredients such as medicines are mixed with excipient and then kneaded together with binder and solvent such as alcohol or water to prepare a wetted paste. A mold is filled with this paste. Top and bottom surfaces of the paste within the mold are coated with powder such as lubricant in order to avoid possible sticking of the paste to the apparatus during a subsequent compression step. Then a compressive pressure is exerted on the surface of the paste. Thereafter, the tablet is taken from the mold. The molded tablet can contain water-soluble or fat-soluble medicine.

12 Claims, 11 Drawing Sheets

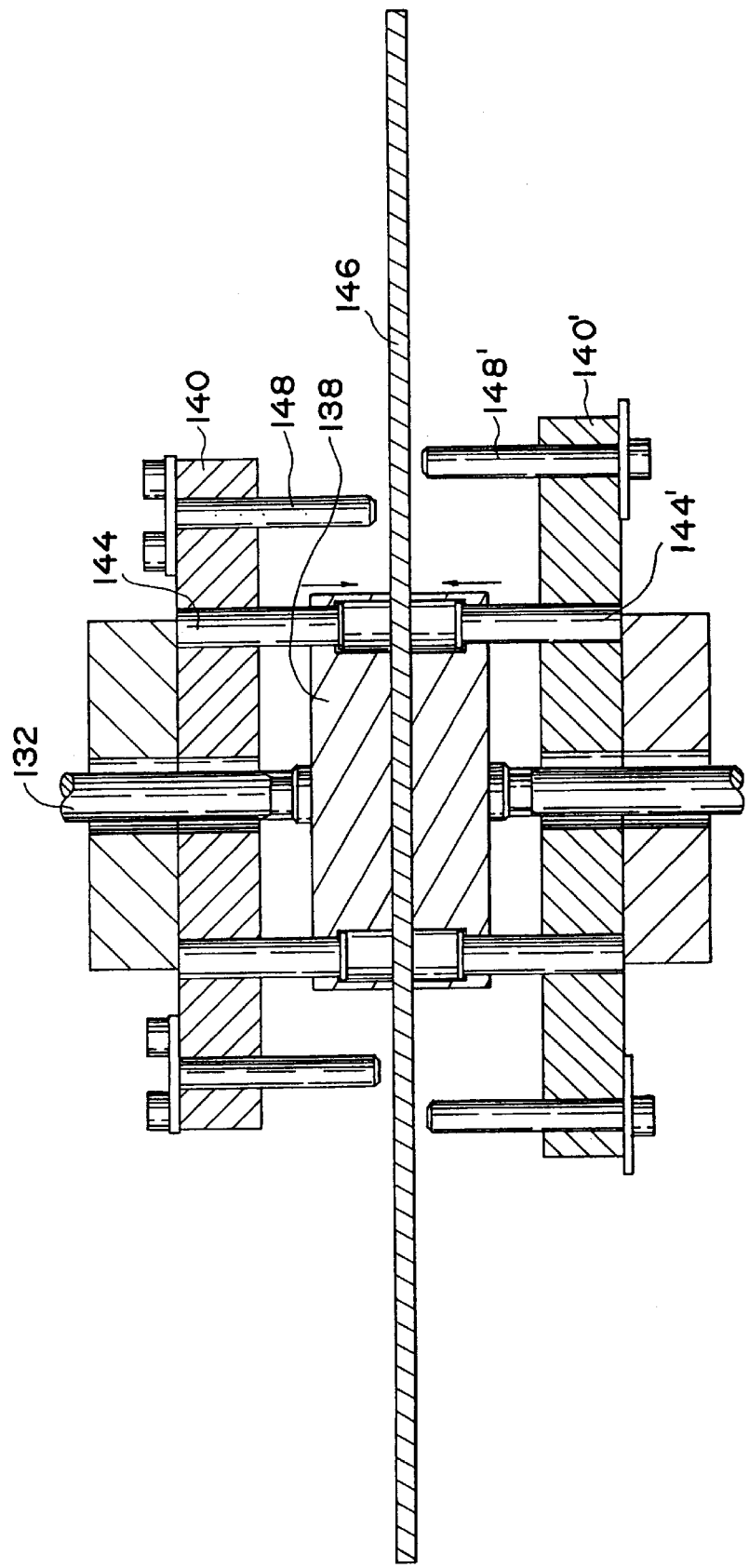

METHOD AND APPARATUS FOR PREPARATION OF MOLDED TABLET AND THEREBY PREPARED MOLDED TABLET

BACKGROUND OF THE INVENTION

This invention relates to method and apparatus for compression molding of paste to obtain a so-called molded tablet.

In general, the aged have weakened corporal, as well as physiological functions, and often suffer from more or less significant dysphagia which makes it difficult to take a dose of medicine. All the dosage forms commonly used such as a tablet, capsule, granule and powder are often inconvenient for the aged in that a dose of medicine sticks in patient's throat and does not go down the patient's throat due to poor salivation and, particularly in the case of a powder or granule, the patient is readily choked with the powder or granule and the power or granule is apt to be caught by artificial teeth.

In view of such problem, various dosage forms have been developed, which maintain traditional convenience of handling which characterizes a tablet, but which can be easily taken without the necessity of water, even by a patient whose ability to swallow is insufficient.

Such improved dosage forms include the buccal tablet and trochiscus, both of which are suitable for patient having poor swallowing ability. So-called molded tablet also has already been developed, which is usually obtained by filling a mold with a solvent-wetted paste and then drying moldings.

Conventionally, the molded tablet is prepared by a method comprising the steps of wetting a mixture of active ingredients, such as medicine and excipient, with a solvent such as alcohol or water, then rubbing this mixture into a mold, taking off the moldings from the mold and thereafter drying the moldings. This method is known commonly as the rub-in method and executed by using an apparatus well known to the art. This well known method is particularly preferable for preparation of a sublingual tablet or the like requiring rapid dissolution, since the tablet prepared by this method includes no compression step and is relatively soft and disintegration as well as dissolution thereof after the tablet has been taken can be correspondingly accelerated.

However, this well known method is disadvantageously limited in regard to the applicable type of medicine. As to both the buccal tablet and the trochiscus, the type of medicine that is applicable thereto is principally water-soluble and dissolution thereof within patient's mouth inconveniently takes a lot of time.

The type of medicine conventionally applicable to the molded tablet also is water-soluble and preparation of the molded tablet containing fat-soluble medicine has not been reported.

Furthermore, the molded tablet is extremely fragile and its mechanical strength is correspondingly low. Due to a high degree of wear and tear (i.e., degree of damage under a physical shock) and destructibility, the molded tablet of the prior art is inconvenient to handle and the active ingredients in each tablet is liable to become uneven. As to handling, the molded tablet of the prior art has been apt to be damaged during a process of packaging or unpacking.

SUMMARY OF THE INVENTION

Accordingly, it is a principal object of the invention to provide molded tablet that guarantees disintegration as rapid as has been guaranteed by the molded tablet of the prior art and has a resistance to wear and tear substantially improved over the molded tablet of prior art.

The object set forth above is achieved, according to the invention, by a specific method for preparation of a molded tablet, comprising steps of filling a mold with solvent-wetted paste and molding said paste under compression.

Filling of the mold with solvent-wetted paste is mechanically or manually preformed.

Said compression of the tablet varies in accordance with size of tablet; however, preferably compression is performed under a pressure of 5 to 100 Kg per tablet. While a punch pin or the like is preferable as the means used for compression, useful means are not limited thereto.

Sticking of the paste to the mold may be avoided by coating a surface of the tablet to be compressed or a surface of a press punch with powder prior to actual compression molding in order to avoid so-called double punching, resulting in poor appearance as well as unevenness of tablet weight and the other drawbacks.

It is possible for the molded tablet prepared by the inventive method to contain not only water-soluble medicine to which the conventional molded tablet has been limited but also water-insoluble and fat-soluble medicine.

Thus the molded tablet of the invention is prepared by molding the solvent-wetted paste in a mold and medicine contained by the molded tablet is not limited to any specific type. However, one of the most important feature of the molded tablet according to the invention lies in that a fat-soluble medicine can be effectively contained therein.

To prepare the molded tablet containing a fat-soluble medicine, the fat-soluble medicine may be mixed with excipient such as mannitol, cane sugar, D-glucose or xylitol and, if necessary, surfactant, corrective flavor etc., then added to the mixture may be a wetting agent such as ethanol and, if necessary, a binder, and thoroughly kneaded together into the form of paste which may be then rubbed into the mold. Moldings may be taken off from the mold and then dried to the desired molded tablet containing therein the fat-soluble medicine.

The term "fat-soluble medicine" used herein refers to medicines which are substantially water-insoluble but easily soluble in an organic solvent, including but not limited to ubidecarenone, tocopheryl nicotinate, teprenone, indomethacinfarnesyl, indomethancin, vitamin E, menadione, menatetrenone, vitamin A, vitamin D and steroid.

The binder may be mixed, in its powdery state, with other ingredients such as an excipient.

In addition to the medicines as mentioned above, the method and the apparatus of the invention can employ the other various medicines to prepare the molded tablet, for example: nicardipine hydrochloride, nifedipine, dihydroergotoxine mesilate, furosemide, spironolactone, loperamide hydrochloride, pantethine, sodium picosulfate, chlormadinone hydrochloride, alphacarcidol, haloperidol, bromocriptine mesilate, glibenclamide, triazolam, diazepam, etizolam, sodium valproate, carbamazepine, ambroxol hydrochloride, planoprofen, sulindac, amoxillin, and erythromycin.

Wetting agents which can be used for the invention include organic solvents such as ethanol, propanol and isopropanol, water, or a mixture thereof, and water-insoluble organic solvents such as hexane.

It is also possible, when any oily medicine is used at room temperature, to powderize such medicine by adsorption on silicic acid anhydride prior to actual use. It is also possible to fill, for example, a seamless capsule of small diameter with such medicine and then to mix this with wet powder before introduced into the mold.

This invention provides an effect as will be described.

As has previously been described, the molded tablet of the invention is prepared by filling the mold with the paste comprising ingredients kneaded together, molding this paste under compression, taking off the moldings from the mold and thereafter drying the moldings. It was found that the molded tablet thus prepared exhibits a degree of wear and tear substantially reduced over the molded tablet of the prior art prepared by the method comprising no step of compression and maintains the desired void volume in each tablet as well as the desired disintegration time. With a consequence, damage of the molded tablet possibly occurring during a process of packaging or the like can be sufficiently reduced to facilitate its handling.

The molded tablet prepared according to the invention to contain a fat-soluble medicine is characterized by its rapid disintegration and even the aged, whose ability of swallowing is generally poor, can take the tablet without the aid of water. In this manner, even the aged, who have more or less difficulty in swallowing a solid matter, can easily take desired medicine.

Rapid disintegration of the inventive molded tablet is achieved even when it contains a fat-soluble medicine due to its substantially high void volume.

The molded tablet prepared by the conventional method exhibits a void volume normally lower than 20%, but the molded tablet of the invention containing fat-soluble medicine exhibits a void volume of 25% or higher. This is due to a particular effect of compression performed in step C as will be described later in regard to the method according to the invention.

In this way, the molded tablet of the invention has a degree of wear and tear substantially reduced over the molded tablet of the prior art, so damage of the molded tablet possibly occurring during a process of packaging or the like is sufficiently reduced to facilitate its handling.

BRIEF DESCRIPTION OF THE DRAWINGS

The above and other objects of the invention will be seen by reference to the description taken in connection with the accompanying drawings, in which:

FIG. 5 is a plan view of powder coating machine serving to coat top and bottom surfaces of the paste with lubricant or the like;

FIG. 12 is an axial sectional view taken along a line XII—XII in FIG. 10.

DETAILED DESCRIPTION OF THE INVENTION

The invention will be described more in details with respect to the accompanying drawings.

Figure 1:
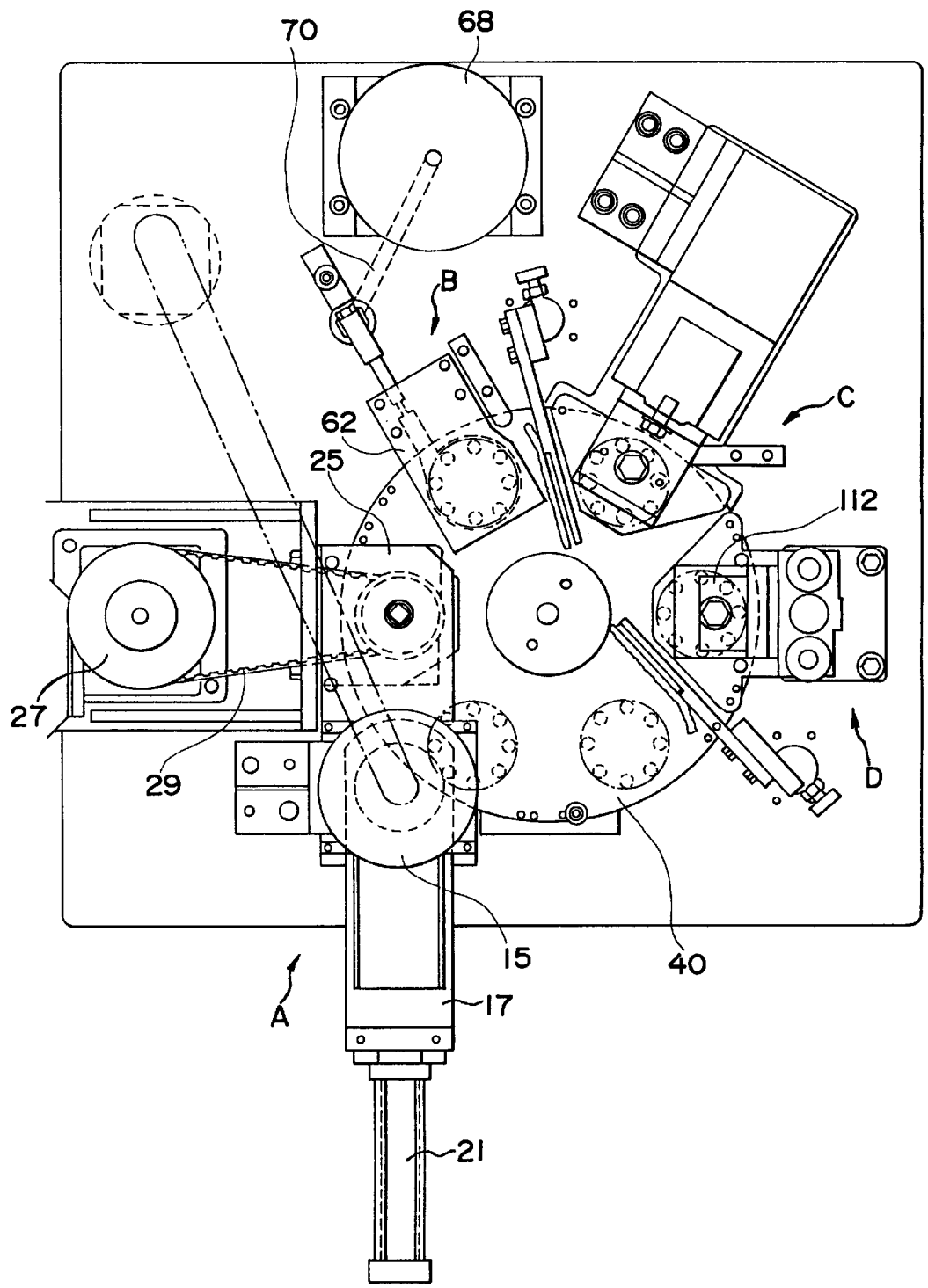
FIG. 1 is a schematic plan view illustrating a specific apparatus used to execute the method of the invention.

Referring first to FIG. 1, a principle of the invention is schematically illustrated in a plan view, in which a reference letter A designates a step of filling a mold with wetted paste, a reference letter B designates a step of coating the paste introduced into the mold with powder, a reference letter C designates a step of compressing the paste within the mold, and a reference letter D designates a step of discharging molded paste.

(Step A)

Figure 2:
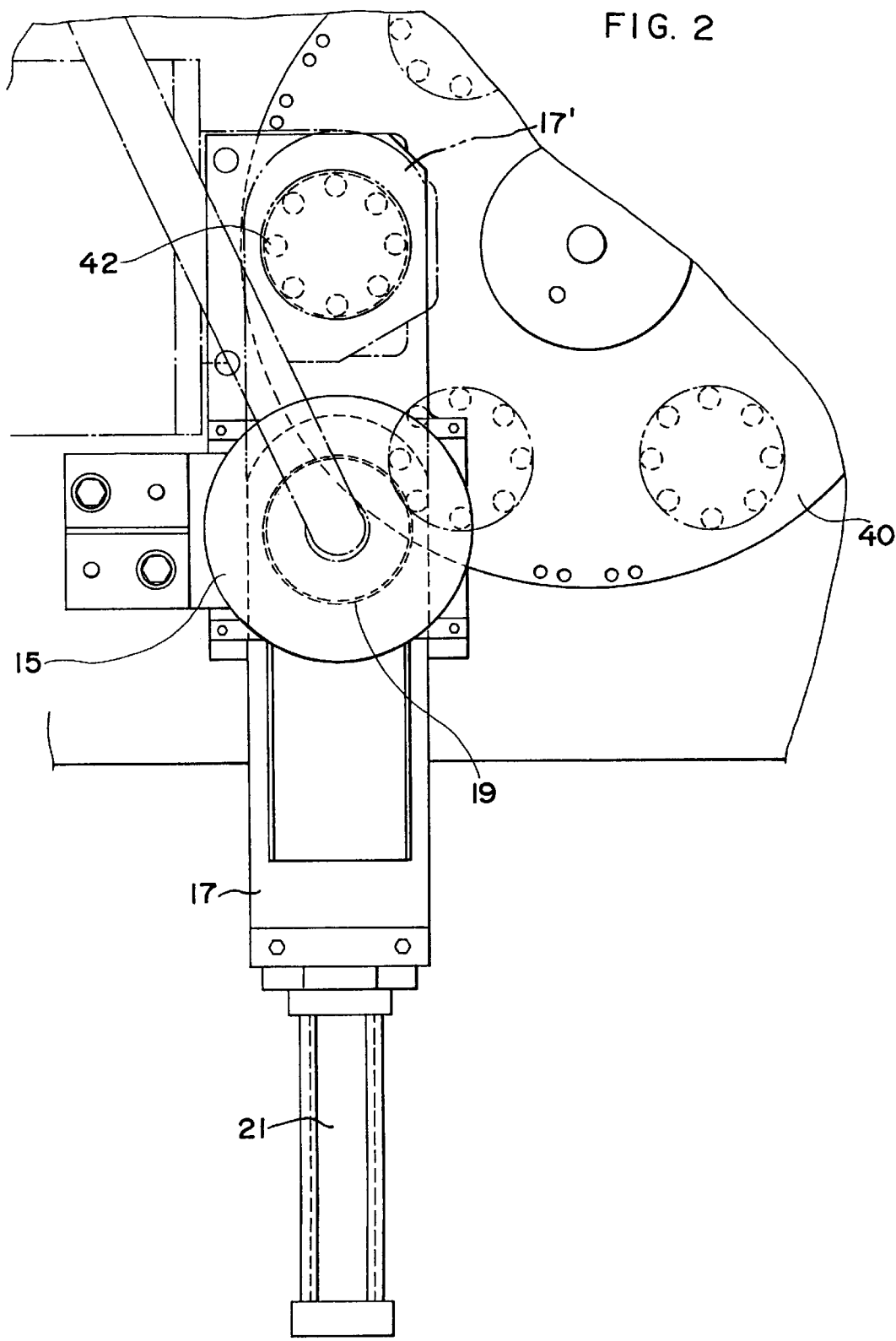
FIG. 2 is a plan view illustrating a step of charging a filling machine with paste as the starting material of the molded tablet by a shuttle.

In the step A, active ingredients such as medicine is mixed with excipient, then kneaded together with binder and solvent such as alcohol or water to obtain wetted paste. The paste falls from a hopper 15 (FIG. 2) provided for storage thereof and fills up a cylindrical cavity 19 of a shuttle 17. The shuttle 17 comprises a thick plate which is rectangular as viewed from above and has a rounded forward end. Rear end of the shuttle 17 is connected to a rod of an air cylinder 21.

Said paste is molded by said cavity 19 of the shuttle 17 into a cylindrical shape. The shuttle 17 is filled with the paste falling from the hopper 15 at a position as indicated by the broken line and then moves to a position as indicated by two-dot-chain line 17' just above a mold 42 on a turntable 40 and just below a filling machine 25. The filling machine 25 has a shaft 31 adapted to be rotatably driven from an electric motor 27 via gears and a belt 29. The shaft 31 fixedly extends through a casing 33 and provided on its forward end with a propeller 35 consisting of four blades.

Figure 3:
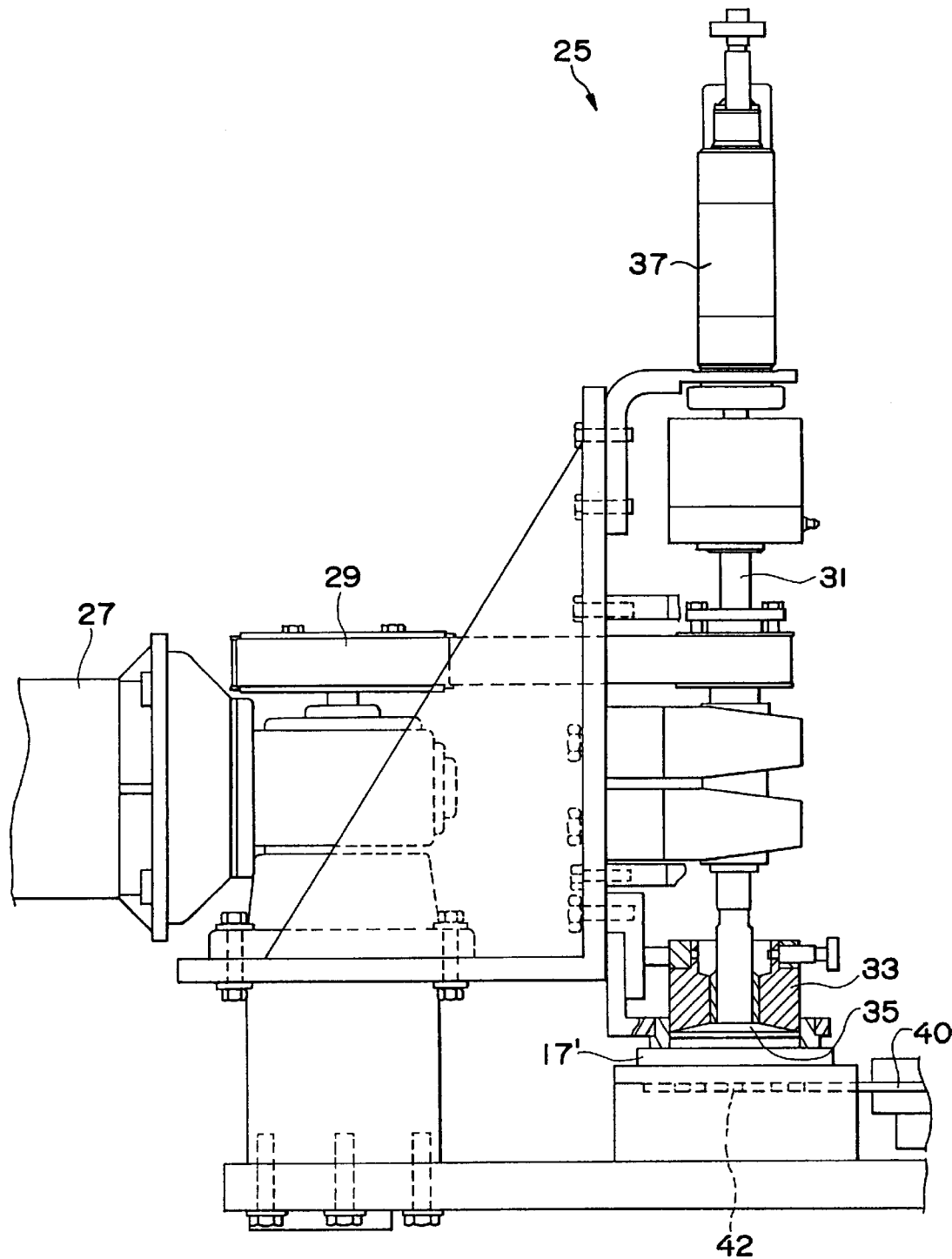
FIG. 3 is a front view of the filling machine serving to fill a mold with said paste.
Figure 4A:
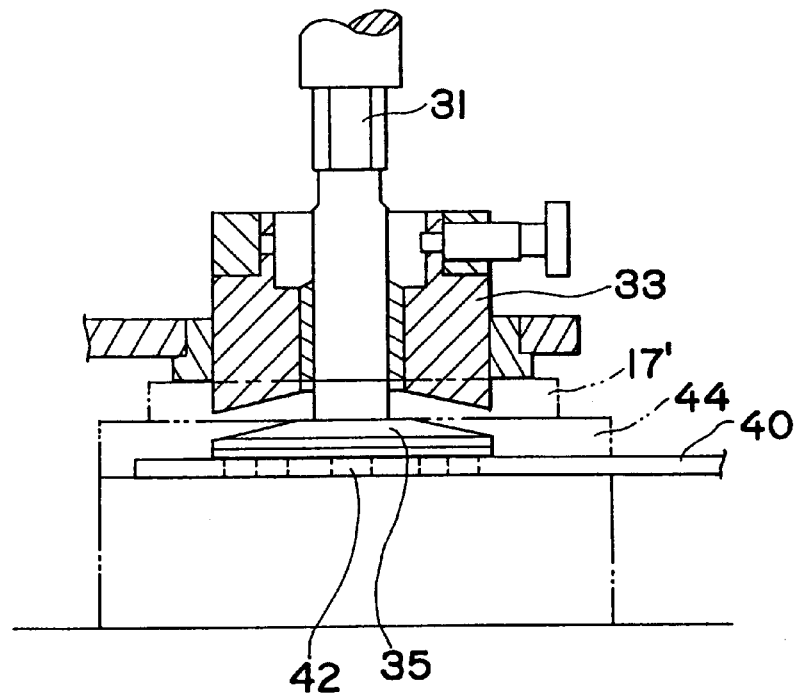
FIG. 4(a) illustrates, in an axial section taken in the proximity of a casing 33, a step of filling the mold with said paste by a propeller.
Figure 4B:
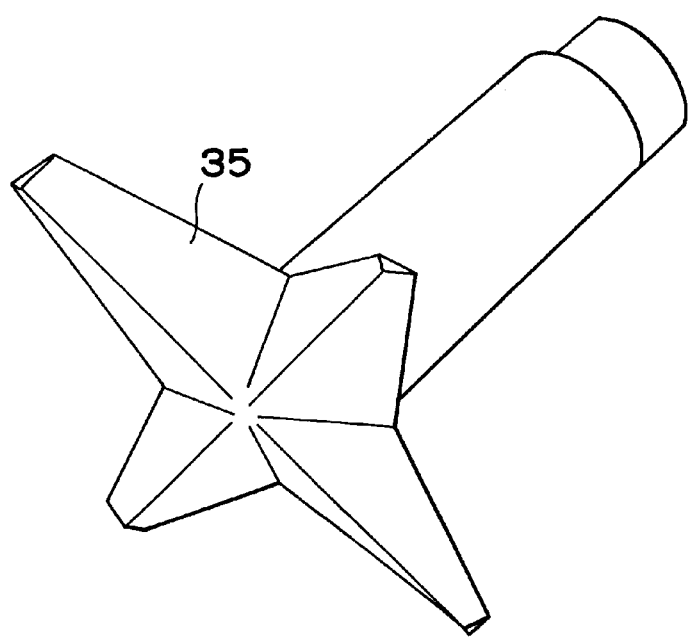
FIG. 4(b) is a perspective view of a propeller illustrated by FIG. 4(a)

Referring to FIG. 3, the shaft 31 is shown as lifted up and in such state the shuttle 17 transfers the paste to this position. Now an air cylinder 37 associated with the filling machine 25 causes the shaft 31 and the propeller 35 to descend. FIG. 4(a) illustrates such state. As said shaft 31 and said propeller 35 descend, the paste within the shuttle 17 is rubbed by the propeller 35 into the mold 42 on the turntable 40. The propeller 35 has its propelling surface appropriately sloped (see FIG. 4(b)) so that the paste may be smoothly rubbed into the mold 42.

It should be understood that, in the illustrated embodiment, the turntable 40 is provided with six groups of the molds 42 arranged circumferentially of the turntable 40 so as to define a concentric circle inside the periphery of the turntable 40, each group including eight molds 42 arranged so as to define a small circle and each molds extends through the turntable 40.

With such arrangement, a circumferential speed of the propeller 35 is kept constant with respect to each mold 42 of each small circle, so that paste can be evenly rubbed into the respective molds 42 and the molded tablet of uniform weight can be prepared.

The paste once rubbed into the molds 42 have their tops cut by rubbing, as the turntable 40 is rotated, by an inner circular groove of a scraper 44 provided stationarily and independently of the turntable 40.

(Step B)

Figure 5:
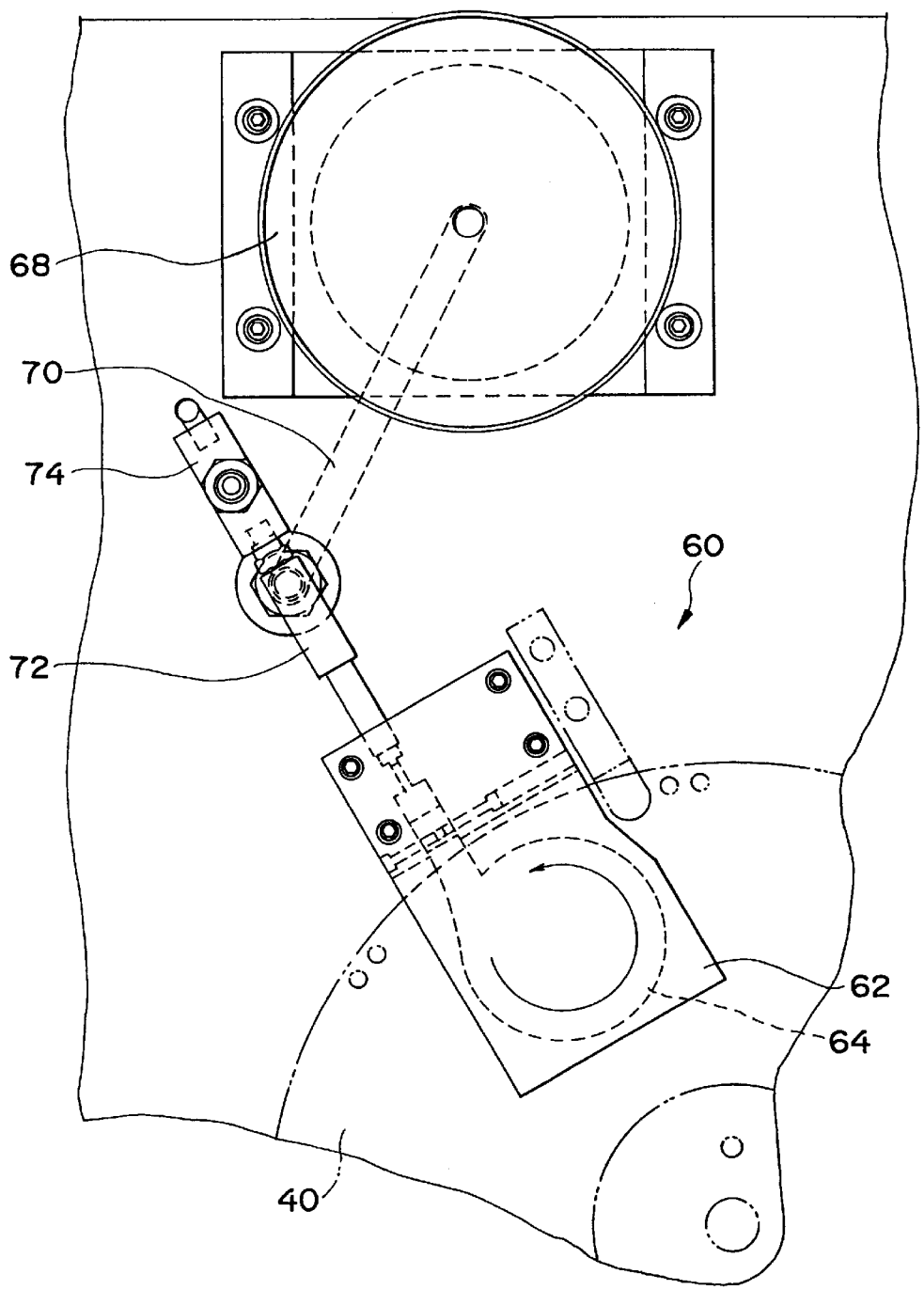
Figure 6:
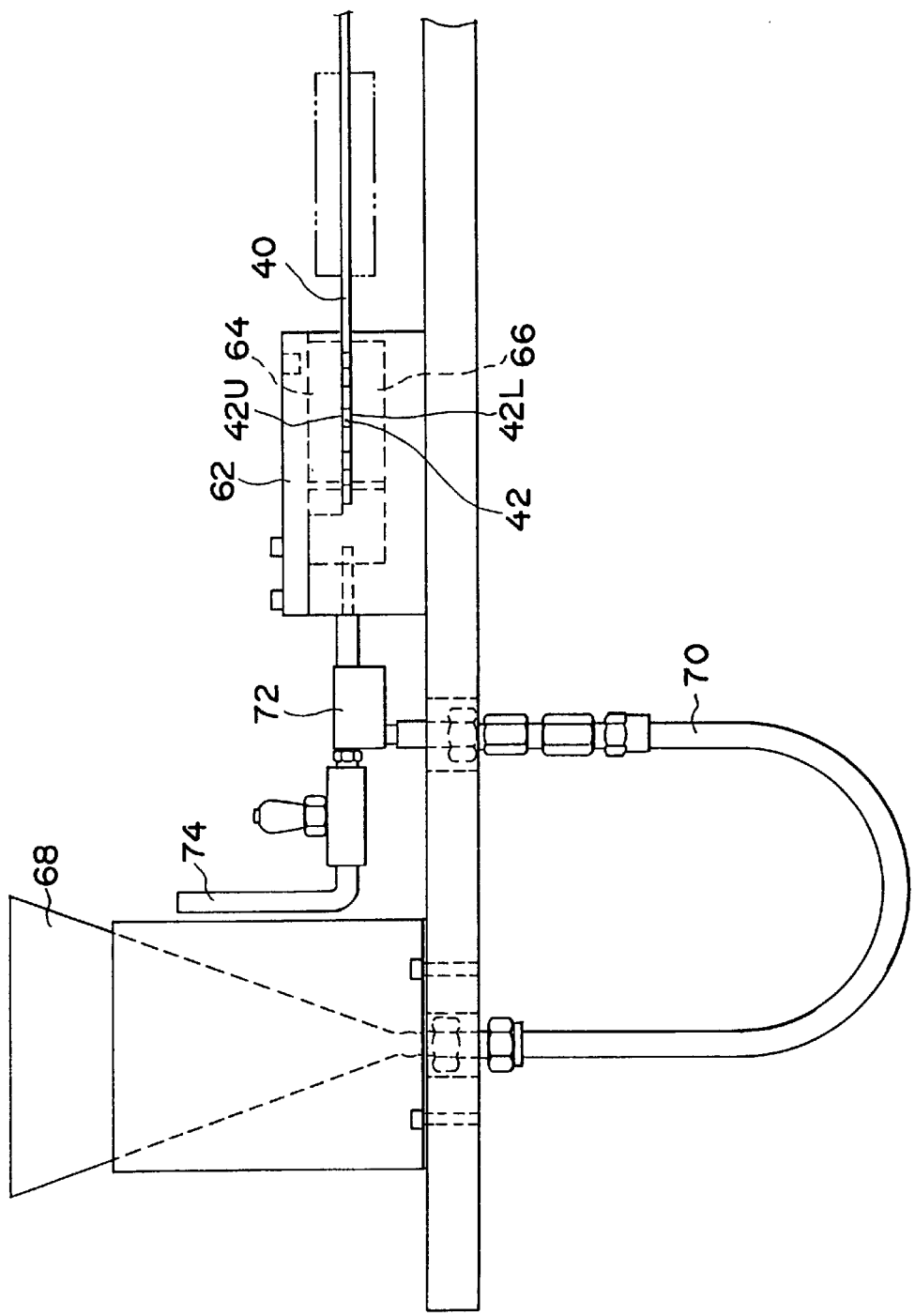
FIG. 6 is a front view of the powder coating machine illustrated by FIG. 5.

The paste rubbed into the molds in the manner as has been mentioned above on the step A is now transported to the step B. On this step B, the top and bottom of the paste within the mold is coated with lubricant or the like. Referring to FIGS. 5 and 6, the step B is illustrated in plan and front views, respectively.

The groups of molds arranged in the concentric circle which have been filled with the paste on the step A reaches a powder coating station 60 serving to coat top and bottom of the paste within the molds with lubricant or the like. The powder coating station 60 includes a shoe 62 defining therein an upper chamber 64 and a lower chamber 66. Top surfaces 42U of the respective molds 42 arranged in the concentric circle on the turntable 40 which have been filled with the paste confront the upper chamber 64 and bottom surfaces 42L of the respective molds 42 confront the lower chamber 66 and the upper chamber 64 as well as the lower chamber 66 are respectively supplied with powder such as a lubricant under a pressure of compressed air so that the powder eventually clings to the top and bottom surfaces of the paste within the molds.

Both the upper chamber 64 and the lower chamber 66 have circular outer peripheries as seen in FIG. 5 and the powder such as a lubricant is rotated circumferentially in a direction as indicated by an arrow.

A reference numeral 68 designates a hopper charged with the powder such as a lubricant. The powder such as a lubricant is transported through a tube 70 to a vacuum conveyor 72. Compressed air is supplied from a pump (not shown) through an air supply station 74 and a mixture of said compressed air and the powder such as lubricant is supplied to the upper chamber 64 and the lower chamber 66 so as to be blasted to the top and bottom surfaces of the paste.

(Step C)

Figure 7:
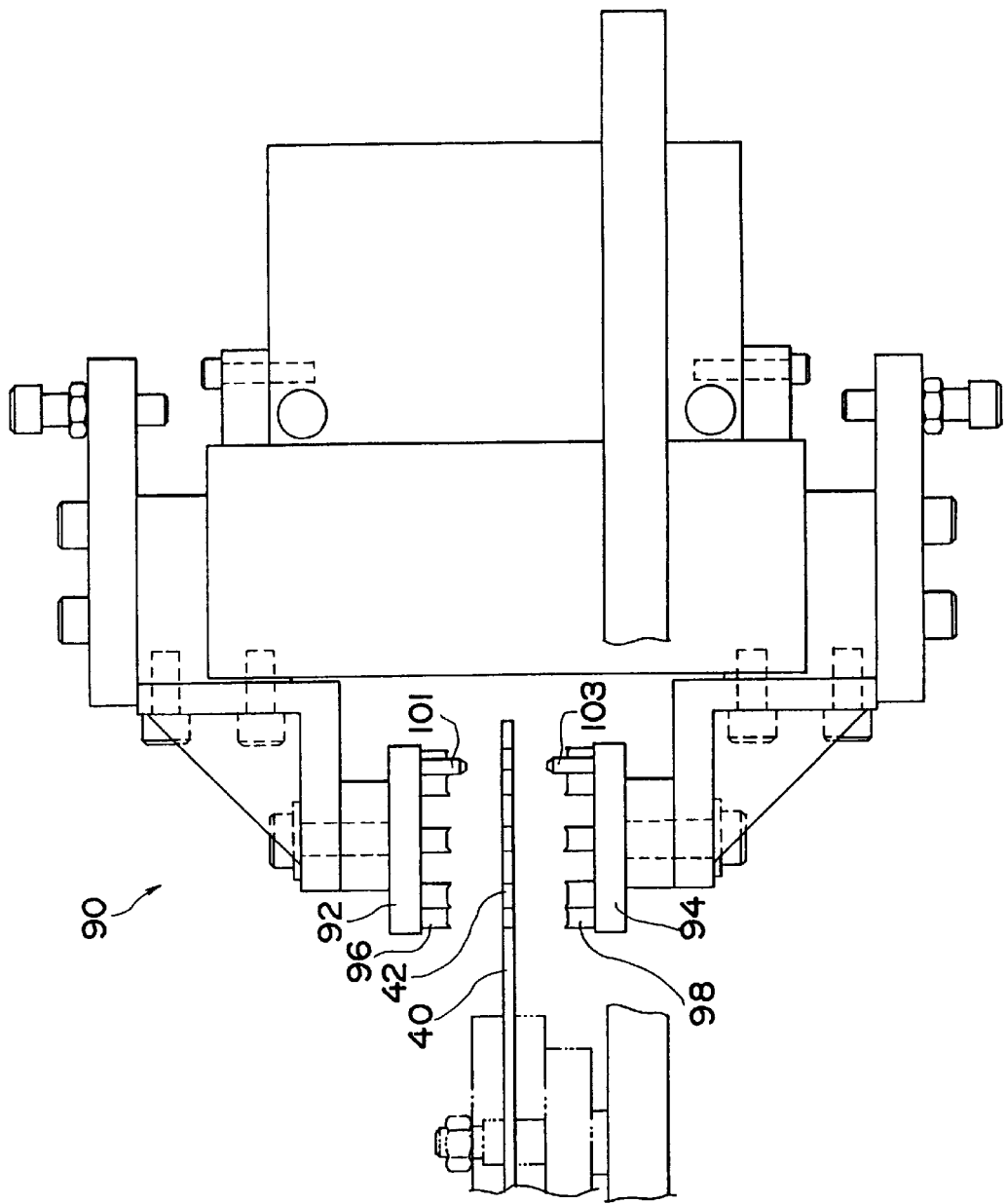
FIG. 7 is a front view of a compressing machine serving to compress top and bottom surfaces of the paste.

The paste thus coated on their top and bottom surfaces with the powder such as a lubricant reaches a compressing station 90 as the turntable 40 is further rotated. Referring to FIG. 7, the compressing station 90 includes an upper punch plate 92 and a lower punch plate 94 above and below the turntable 40, respectively. The upper punch plate 92 and the lower punch plate 94 are provided with an upper punch pins 96 an a lower punch pins 98, respectively. An air cylinder (not shown) causes the upper punch plate 92 and the lower punch plate 94 to approach to each other to compress the paste within the respective molds. At this time point, a tapered forward end of a guide pin 101 is located below the forward end of the upper punch plate 92 while a forward end of a guide pin 103 is located above the upper end of the lower punch plate 94 so that the respective forward ends of the guide pins reach guide holes (not shown) formed in the turntable before the respective forward ends of the upper punch pins 96 and the lower punch pins 98 reach them. The tapered configuration of these guide pins allows both the upper punch pins 96 and the lower punch pins 98 to be properly guided on the associated molds.

Both the upper punch pins and the lower punch pins have their forward ends in the form of trapezoidal cavities so that each tablet may be molded to have trapezoidal top and bottom which contribute to high resistance to wear and tear of the molded tablet.

(Step D)

Figure 8:
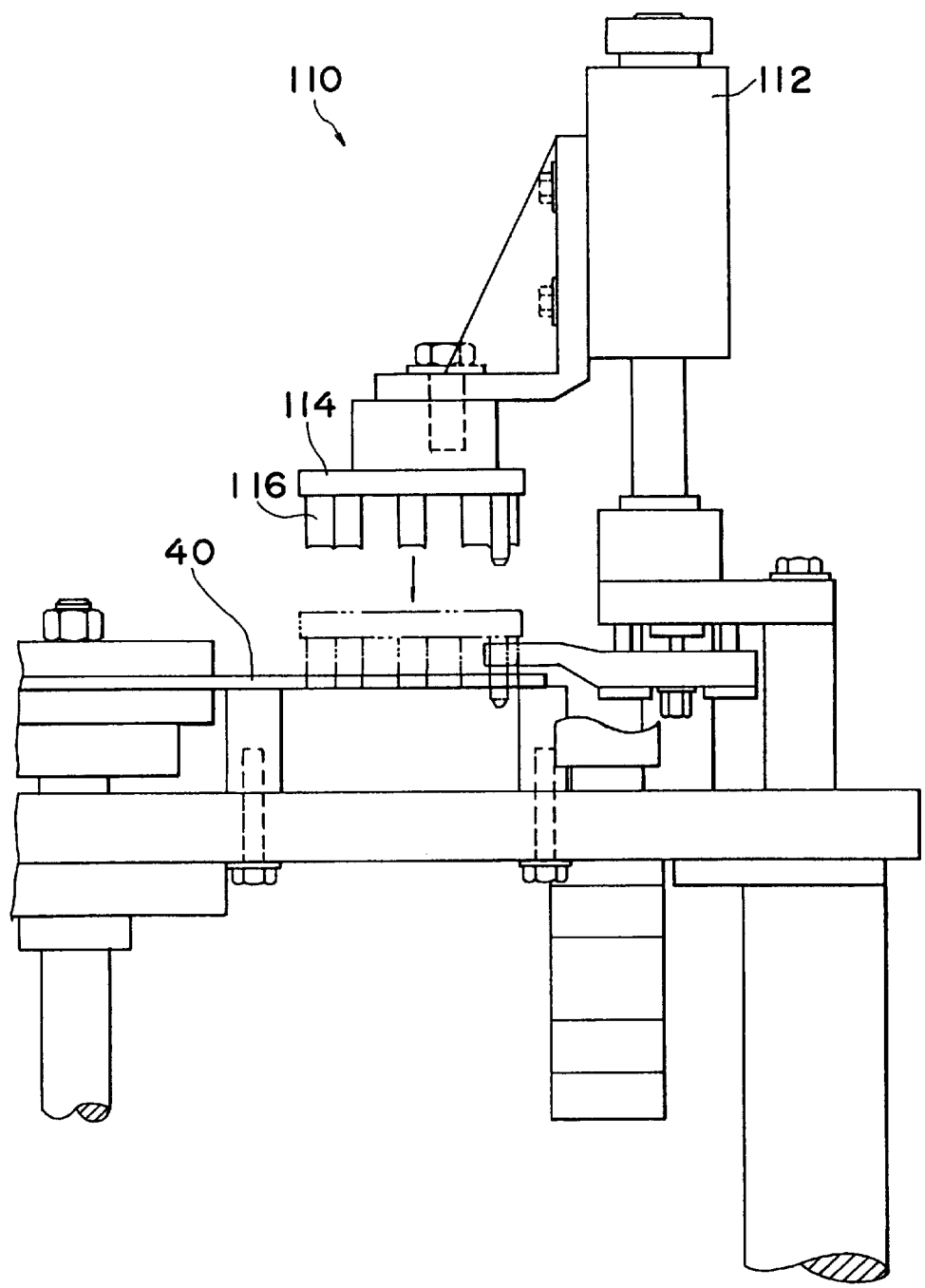
FIG. 8 is a front view of a paste discharging machine.

The respective molds 42 arranged in a concentric circle and filled with the paste which has been compressed by the punch pins of the compressing station 90 then reach a discharging station 110 illustrated by FIG. 8 The discharging station 110 serves to discharge the moldings from the respective molds. The respective molds 42 then reaches a punching machine 112. The punching machine 112 includes a punch plate 114 located above the turntable 40. The punch plate 114 is provided, in turn, with punch pins 116 adapted to be lowered by an air cylinder (not shown) so as to punch the tablets within the respective molds arranged in the turntable 40. The molded tablets thus punched fall onto a belt (not shown) or the like and thereby conveyed to the subsequent step.

(Details of Step B)

Outlines of the respective steps A through D have been described above. Now the step B will be described more in details. When a step of compression is employed in preparation of the molded tablet as in the method according to this invention, the molded tablet sometimes entirely or partially sticks to the punch surface immediately after the step of compression, resulting in so-called double punching, poor appearance and weight unevenness of the product. Particularly, said double punching is a serious problem since it might lead even to damage of the apparatus and the poor appearance is also a serious problem in view of the product quality. Unevenness of weight might result in excess or deficiency of desired content of the active ingredients which is a serious problem in view of the safety.

From these viewpoints, there is provided the step of coating the wet paste with powder prior to the step of compression in order to avoid sticking of the paste to the punch pins during the step of compression.

Figure 9A:
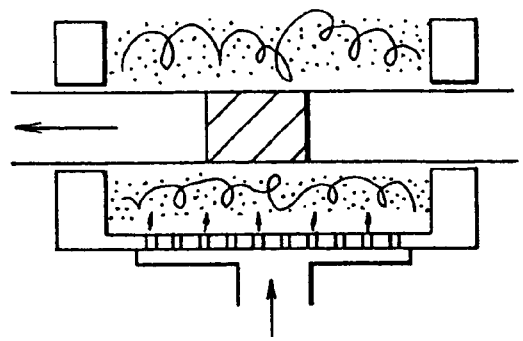
FIG. 9 (a) through (c) is a front view illustrating another embodiment of the powder coating machine.
Figure 9B:
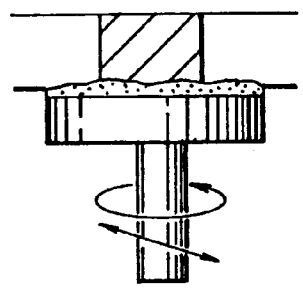

The powder coating machine may be of any type so far as it is a machine able to coat the top and bottom surfaces of the paste with powder and not limited to the machine adapted to be supplied with the powder such as a lubricant by a pneumatic conveyor and to spray the powder onto the top and bottom surfaces of the paste. Referring to FIG. 9, there are illustrated alternative embodiments of the powder coating machine. More specifically, it is possible to spray the powder onto the top surface of the paste by the pneumatic conveyor and to spray the powder onto the bottom surface by bubbling, as illustrated by FIG. 9(a). Alternatively, each surfaces of the paste may be coated by a rotatable or reciprocating brush with the powder as illustrated by FIG. 9(b).

Figure 9C:
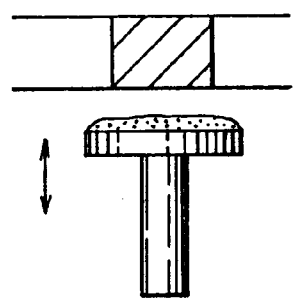
Figure 10:
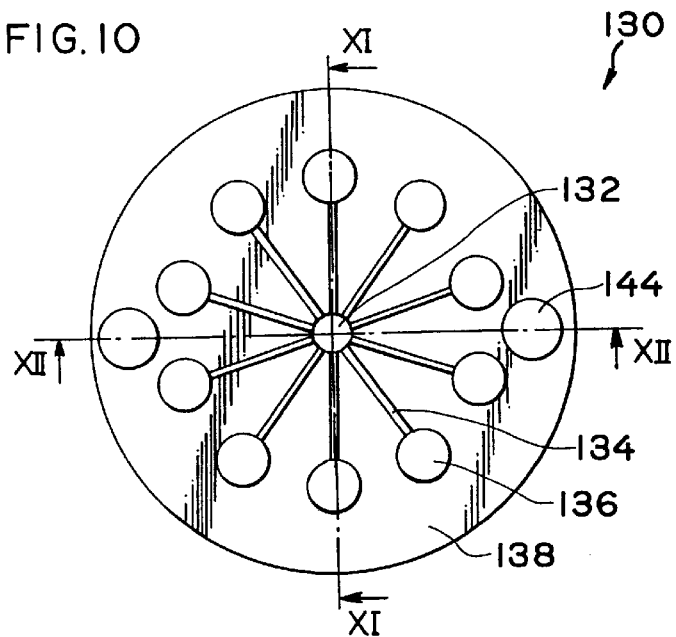
FIG. 10 is a plan view of a combined powder coating/compressing machine.

Referring to FIG. 9(c), it is also possible to coat each surface of the paste with the powder such as a lubricant utilizing a brush which is vertically movable. Coating with the powder may be also performed during the step of compression as illustrated by FIG. 10 or FIG. 12 and then it may be the press punches rather than the surfaces of the paste that is coated with the powder.

The powder used for the step B is not limited to any specific type so far as it is effective to avoid sticking of the tablet to the mold and the powdery lubricant or the like is preferable. However, the powder for coating is not limited to said lubricant and various types of powder may be effectively used for this purpose, for example, stearic acid, calcium stearate, magnesium stearate, talc, cellulose, saccharoid, starches such as corn starch and silicic acid anhydride and, among them, stearic acid, calcium stearate, magnesium stearate and starches such as corn starch and potato starch are particularly preferable. It is obviously possible to use a mixture of these compounds.

It should be noted here that the paste used for preparation of the molded tablet is wetted with solvent and the lubricant can not properly function if it is kneaded into the paste as in preparation of ordinary tablet. The invention solves this problem by coating the top and bottom surfaces of the paste after it has been rubbed into the mold with the powder such as a lubricant so as to prevent the paste from sticking to the punch pin during the step of compression.

(Details of Step C)

Now details of the step C will be described.

Conventionally the molded tablet has been prepared by rubbing wet powder into a mold, taking off the tablet from the mold and drying it. The tablet prepared by such method has been too fragile to be easily handled. On the contrary, the inventive method prepares the tablet by filling the mold with the mixture of ingredients kneaded together in the form of paste, molding it under a compression, taking off the tablet from the mold and drying it. The tablet prepared by such method can be much more easily handled over the conventional product prepared by the method including no step of compression.

Depending on various factors such as type of medicine and/or excipient and shape and/or size of tablet to be molded, the compressing pressure is preferable 5 to 100 Kg per tablet and more preferably of 10 to 50 Kg per tablet. The molded tablet of the invention can be prepared by automatically or manually filling the mold of open type with the paste.

(Machine Adapted to Perform the Step B in Combination With the Step C.)

Figure 11:
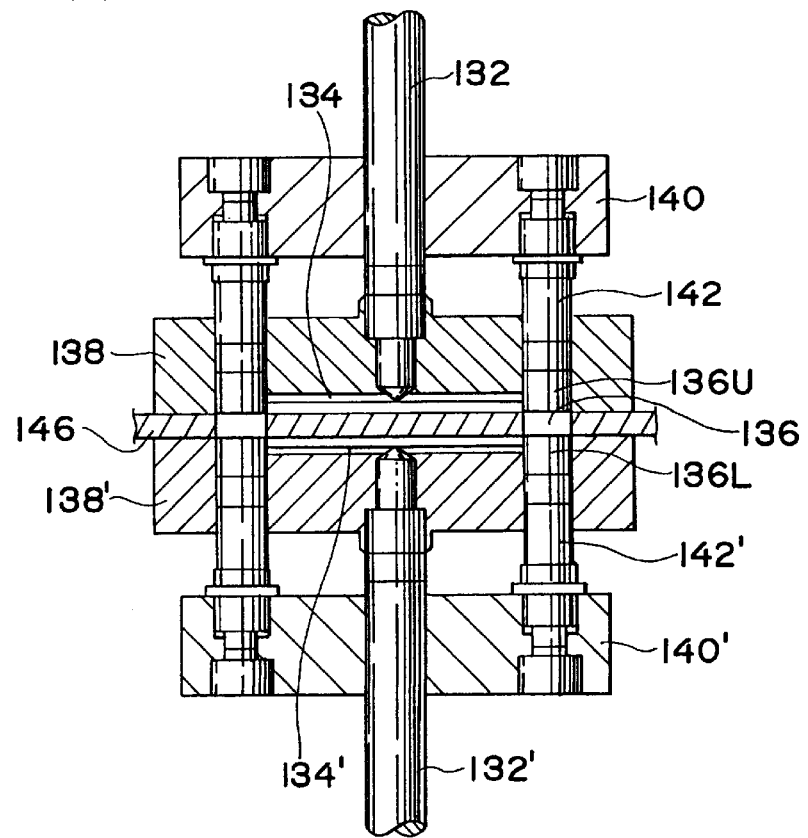
FIG. 11 is an axial sectional view taken along a line XI—XI in FIG. 10.

Referring to FIGS. 10 through 12, there is illustrated an embodiment of the machine or station in which the steps B and C are combined together.

FIG. 10 is a plan view of a combined powder coating/compressing machine 130, in which a reference numeral 132 designates a vertical pipe to supply powder such as a lubricant and compressed air, a reference numeral 134 designates pipes radially extending from said vertical pipe 132 to supply said powder and air towards the spaces above and below respective molds and a reference numeral 136 designates molds. Ten molds are arranged so as to define a circle which is concentric with the turntable, each of said molds extending through the turntable.

FIG. 11 is an axial sectional view taken along a line XI—XI in FIG. 10. Above and below each mold, there are provided chambers 136U, 136L of a same cross-sectional shape as the mold, respectively. Compressed air is supplied through the vertical pipe 132 and the radial pipes 134 into the respective chambers 136U, 136L so as to be blasted onto top and bottom surfaces of the paste within each tablet. A reference numeral 138 designates blocks defining therein said chambers 136U, 136L, respectively. Then an upper punch plate 140 carrying punch pins 142 and a lower punch plate 140' carrying punch pins 142' approach each other to compress the paste from above and below the mold and thereby to mold a desired tablet.

FIG. 12 is an axial sectional view taken along a line XII—XII in FIG. 10, in which a reference numeral 144 designates compression springs serving to bias the respective blocks against the turntable 146. A reference numeral 148 designates a guide pin serving to guide the punch pins carried by the punch plate 140 towards above the associated molds.

In this way, the steps B and C are effectively combined and correspondingly accelerated to improve the productivity.

(Molded Tablet)

As will be apparent from the foregoing description, the invention is characterized by the additional step of compression in preparation of the molded tablet and applicable to preparation of the molded tablet whether it should contain water-soluble medicine or fat-soluble medicine.

(Molded Tablet Containing Fat-Soluble Medicine)

Preparation of the molded tablet containing fat-soluble medicine employing the step of compression according to the invention will be described in reference with several Examples and a Control.

EXAMPLE 1

10 g of ubidecarenone, 30 g of mannitol and 1 g of sucrose fatty acid ester were mixed together, then 40 ml of ethanol solution in which 2 g of polyvinylpyrrolidone had been dissolved was slowly added to said mixture. A mold having a diameter of 10 mm and a thickness of 5 mm was filled with this mixture, then a pressure of 20 Kg was exerted on the mixture, the molded mixture was taken off from the mold and dried to obtain a tablet containing ubidecarenone.

The molded tablets prepared in the same manner as in Example 1 but by varying the type of excipient and the level of compressing pressure exhibited the void volumes and the disintegration times as shown in Table 1. In the Table 1, compressing pressure of 500 (Kg/Tab) indicates that the molded tablet containing mannitol was prepared by the conventional method under a compressing pressure of 500 Kg/Tab.

TABLE 1

| Excipient | Compress pressure (Kg/Tab) | void volume | Disintegration time (min) |
|---|---|---|---|
| Sucrose | 10 | 31.3 | 1.3 |
| Mannitol | 10 | 36.8 | 0.6 |
| Maltitol | 20 | 31.5 | 1.6 |
| Xylitol | 10 | 32.9 | 1.1 |
| Maltitol | 10 | 46.6 | 0.5 |
| Glucose | 10 | 34.6 | 1.1 |
| Sorbitol | 40 | 35.4 | 0.6 |
| Mannitol (Control) | 500 | 18.3 | 4.4 |

Table 1 indicates that the molded tablet prepared by the method of the invention exhibits higher void volume and more rapid disintegration time than the compressed tablet prepared by the conventional method.

Void volume is calculated by the following formula;

$$\text{Void volume } (\%) = (1 - W/PV) \times 100$$

where

W: weight of a molded tablet after being dried

P: density of dried powder of a molded tablet($g/cm^3$)—measured by Beckmann's pneumatic density meter V: volume of a molded tablet after being dried—figured out by measuring diameter and thickness of tablet using vernier caliper Disintegration time is measured according to Japan Pharmaceutical Condex.

EXAMPLE 2

5 g of ubidecarenone, 150 g of maltitol and 0.5 g of sucrose fatty acid ester were mixed together, then 30 ml of ethanol solution in which 1 g of polyvinylpyrrolidone had been dissolved was slowly added to said mixture. A mold having a diameter of 10 mm and a thickness of 5 mm was filled with this mixture, a pressure of 40 Kg was exerted on the mixture, molded mixture was taken off from the mold and dried to obtain a tablet containing ubidecarenone.

EXAMPLE 3

1 g of teprenone was adsorbed on 5 g of silicic acid anhydride, then mixed with 25 g of xylitol and 0.5 g of sucrose fatty acid ester, and slowly added with ethanol solution containing 0.1 g of hydroxypropylcellulose dissolved therein and mixed together. A mold having a diameter of 10 mm and a thickness of 5 mm was filled with this mixture, the molded mixture was taken off from the mold and dried to obtain a tablet containing teprenone.

EXAMPLE 4

10 g of ubidecarenone, 300 g of mannitol and 1 g of sucrose fatty acid ester were mixed together, thereafter slowly added with 40 ml of ethanol/water (6:4) solution in which 2 g of polyvinylpyrrolidone had been dissolved and mixed together. A mold having a diameter of 10 mm and a thickness of 5 mm was filled with this mixture, a pressure of 20 Kg was exerted on the mixture, the molded mixture was taken off from the mold and dried to obtain a tablet containing ubidecarenone.

EXAMPLE 5

2.5 g of triazolam and 2,968 g of mannitol were mixed together, then 360 g of 60% ethanol solution in which 30 g of polyvinylpyrrolidone had been dissolved was added to said mixture and kneaded together for 15 minutes. A mold having a diameter of 10 mm an a thickness of 4.5 mm was filled with this mixture, a pressure of 20 Kg was exerted on the mixture, molded mixture was taken off from the mold and dried to obtain a tablet containing 2.5 mg of triazolam per tablet.

EXAMPLE 6

2.5 g of sodium picosulfate was mixed together instead of 2.5 g of toriazolam of Example 5 and compressed in the same condition of Example 5. Molded mixture was taken off from the mold and dried to obtain a tablet containing 2.5 g of picosulfate per tablet.

EXAMPLE 7

10 g of haloperidol and 2,960 g of mannitol were mixed together, then 360 g of 60% ethanol solution in which 30 g of polyvinylpyrrolidone had been dissolved was added to said mixture and kneaded together for 15 minutes. Said mixture was molded with the same mold of Example 5 and compressed in the same condition of the Example 5 and dried to obtain a tablet containing 5 mg of haloperidol per tablet.

(Control)

10 g of ubidecarenone, 300 g of mannitol and 1 g of sucrose fatty acid ester were mixed together, then slowly added with 40 ml of ethanol/water (6:4) solution in which 2 g of polyvinylpyrrolidone had been dissolved and mixed together. A mold having a diameter of 10 mm and thickness of 5 mm was filled with this mixture, the molded mixture was taken off from the mold and dried to obtain a tablet containing ubidecarenone.

Void volumes, hardnesses, degrees of wear and tear and disintegration times exhibited by the respective tablets prepared in Examples 1 and 4 and Control are shown in Table 2.

TABLE 2

| Example & Control | Pressure (Kg) | Void Volume (%) | Hardness (Kg) | Wear & tear (%) | Disintegration time (min) |
| --- | --- | --- | --- | --- | --- |
| Example 1 | 20 | 33.4 | 2.6 | 1.7 | 0.6 |
| Example 4 | 20 | 31.5 | 3.4 | 0.7 | 0.6 |
| Control | 0 | 37.5 | 2.0 | 7.6 | 0.5 |

As will be apparent from Table 2, the degree of wear and tear can be significantly reduced by compressing the mixture paste after the mold has been filled with this mixture paste without being accompanied by reduction of the void volume and prolongation of the disintegration, i.e., loss of ease to take the tablet. Consequently, damage of the molded tablet possibly occurring during a process of packaging or the like can be sufficiently reduced to facilitate its handling.

It should be understood that the orientation in which the apparatus, particularly the turntable is installed is not critical. Namely, the turntable may be installed in horizontal, vertical or sloped orientation.

Said hardness was measured by Kiya method hardness meter.

Wear and tear was measured by the test equipment measuring wear and tear of a tablet (product of Sugaki Irika Kogyo Co., Ltd.). Test was held by rotating 20 tablets at 25 rpm for 4 minutes.

While the invention has been particularly shown and described with reference to preferred embodiment thereof, it will be understood by those skilled in the art that the foregoing and other changed in forms and details can be made therein without departing from the spirit and scope of the invention.

What is claimed is:

1. In a method of preparing a molded, rapid disintegration human ingestible tablet where a mold cavity is filled with a wetted paste of material forming the tablet to shape the wetted paste into a wetted tablet, the wetted tablet is removed from the mold cavity and dried to a rapid disintegration tablet, the improvement comprising compressing the wetted tablet while in the mold cavity at a pressure of 5 to 100 Kg per 10 mm of tablet diameter.

2. Method for the preparation of a molded tablet according to claim 1, wherein top and bottom surfaces of each wetted tablet are coated with a powder prior to compressing the wetted tablet such as to avoid sticking of the wetted tablet to the mold cavity during the compression step.

3. Method for the preparation of a molded tablet according to claim 1, wherein surfaces of a compression punch used to perform the compression step are coated with a powder such as to avoid sticking of the wetted tablet to the compression punch.

4. Method for the preparation of a molded tablet according to claim 1, wherein the mold cavity is filled with the wetted paste by rubbing the paste into the mold cavity.

5. Method for preparation of a molded tablet according to claim 1, wherein the compression is at a pressure of 10 to 50 Kg per tablet.

6. Method for the preparation of a molded tablet according to claim 1, wherein the material forming the tablet contains a medicine.

7. Method for the preparation of a molded tablet according to claim 6, wherein the medicine is a fat-soluble medicine.

8. Method for the preparation of a molded tablet according to claim 1, wherein the material forming the tablet contains at least one of an excipient, surfactant, flavor, wetting agent and binder.

9. Method for the preparation of a molded tablet according to claim 1, wherein the compression step is at a pressure such as to produce a void volume in the dried tablet of at least 25%.

10. Method for the preparation of a molded tablet according to claim 2, wherein the powder is at least one of stearic acid, calcium stearate, magnesium stearate, talc, cellulose, saccharoid, starch and silicic acid anhydride.

11. Method for the preparation of a molded tablet according to claim 3, wherein the powder is at least one of stearic acid, calcium stearate, magnesium stearate, talc, cellulose, saccharoid, starch and silicic acid anhydride.

12. Method for preparing a rapid disintegration tablet, comprising the steps of:

(1) filling a mold cavity with wetted powder;

(2) coating surfaces of the wetted powder while in the mold cavity with a lubricant;

(3) exerting a pressure of 5 to 100 Kg per 10 mm of tablet diameter on the wetted powder while in the mold cavity to compress the wetted powder;

(4) pushing the compressed wetted powder as a tablet out of the cavity mold; and (5) drying the tablet.

* * * * *